United States Patent [19]

Duffett

[11] Patent Number: Plant 6,061

[45] Date of Patent: Dec. 15, 1987

[54] CARNATION PLANT NAMED ACE HIGH

[75] Inventor: William E. Duffett, Salinas, Calif.

[73] Assignee: Yoder Brothers, Inc., Barberton, Ohio

[21] Appl. No.: 792,989

[22] Filed: Oct. 30, 1985

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Schwartz, Jeffery, Schwaab, Mack, Blumenthal & Evans

[57] ABSTRACT

A carnation plant named Ace High which is an X-radiation induced color mutation from the commercial cultivar Ace, disclosed in U.S. Plant Pat. No. 4,667. The singular distinguishing trait of Ace High is the extent, distribution and intensity of the color pattern comprised of variegated light orange and scarlet red.

2 Drawing Figures

The present invention comprises a new and distinct cultivar of *Dianthus caryophyllus*, Linn., named Ace High.

Ace High is a product of a planned mutation induction program which had the objective of creating new spray type carnation cultivars expanding the color range of the best commercial cultivars with fast flowering response, unrestricted breaking action, vigorous growth, strong, non-brittle stems, high bud and flower count, and attractive, durable flowers for year-around commercial production.

Ace High was originated from X-radiation applied to the cultivar Ace, disclosed in U.S. Plant Pat. No. 4,667. Ace High was discovered and selected by William E. Duffett on Mar. 16, 1979 in a controlled environment in Salinas, Calif. as one flowering plant within a population of plants propagated from stock plants of the parent cultivar which had been irradiated as cuttings with an X-ray dose of 6000 rads.

The first act of asexual reproduction of Ace High was accomplished when vegetative cuttings were taken from the initial selection in June of 1979 in a controlled environment in Salinas, Calif. by a technician working under formulations established and supervised by William E. Duffett.

Horticultural examination of selected units initiated in March of 1980 has demonstrated that the combination of characteristics as herein disclosed for Ace High are firmly fixed and are retained through successive generations of asexual reproduction.

Ace High has not been observed under all possible environmental conditions. The phenotype may vary significantly with variations in environment such as temperature, light intensity and day length. The following observations, measurements and comparisons describe plants grown in Salinas, Calif. under greenhouse conditions which approximate those generally used in commercial practice.

The following traits have been repeatedly observed and are determined to be basic characteristics of Ace High which in combination distinguish this carnation as a new and distinct cultivar:

1. Commercial double flower type.
2. Flat flower form, reflexing slightly at maturity.
3. Miniature flower size, ranging from 45 to 65 mm. in diameter.

4. Light orange flower color with a scarlet red picotee and striped variegated pattern.
5. Medium flowering response ratings.
6. Six to eight flowers and buds showing color per flowering stem.
7. Medium peduncle length, ranging from 10 to 12 cm.
8. Tall plant height, 60 to 65 cm.
9. Long, strong stems and peduncles.
10. Slight spice fragrance.

Among the commercially available carnations known to the present inventor, the most similar in comparison to Ace High is Ace, disclosed in U.S. Plant Pat. No. 4,667. Reference is made to attached Chart A which compares selected characteristics of Ace with the new cultivar.

Generally, Ace High is similar to Ace in all respects except color. The scarlet red is its major distinguishing trait. Scarlet red variegation of Ace High is significantly more intense and extended in its distribution over the surface of the petals. Ace High develops more and broader stripes and picotee (petal edge) bands of scarlet red color.

In the accompanying photographic drawings,

Sheet 1 is a color photograph showing typical inflorescence and leaf characteristics of Ace High, with colors as nearly true as possible with illustrations of this type.

Sheet 2 is a black and white photograph showing views of the upper, under and side surfaces of the inflorescence.

In the following descriptions, color references are made to The Royal Horticultural Society Colour Chart. Color values were determined between 11:30 a.m. and 12:00 noon on Dec. 20, 1984 under 380 foot-candle light intensity at Salinas, Calif.

Classification:

*Botanical.*—*Dianthus caryophyllus*, Linn. cv Ace High.

*Commercial.*—Miniature carnation for cut spray flower production.

INFLORESCENCE

Flowering response: Medium; initial harvest is 25 weeks from early July plantings grown pinched in Salinas, Calif.

Inflorescence type: Commercial double.

Number of buds and flowers per stem: 6 to 8 with color on first cut; develops a compound spray with 1 to 4 buds per lateral.

Peduncle length: 10 to 12 cm.

Peduncle strength: Strong, seldom brittle.

FLOWER

Size: 45 to 65 mm. diameter.

Type: Commercial double in comparison to single or bullhead.

Petal edge: Flat, slightly reflexed at maturity.

Petal count: 25 to 35.

Petal size: Average length 4.5 cm.; average width 1.5 cm.

Bud shape: Oval, pointed.

Splitting tendency: Slight.

Slab tendency: None.

Keeping quality: On plant, up to 18 days; when cut, up to 12 days at room temperature of 20° C.

Fragrance: Slight spice fragrance.

REPRODUCTIVE ORGANS

Androecium: Filaments 15 to 20, anthers 15 to 20, pollen scant.

Gynoecium: Styles 2, stigmas 2, length 10 to 15 mm.

COROLLA COLOR

General tonality from a distance of three meters: Light orange, picotee scarlet.

Upper surface: 29C, 29B flushed with 36A; picotee edge 42A–C.

*Base.*—1C.

Under surface: 29C flushed with 36B.

*Base.*—1C.

Color stability: Stable color.

Seasonal variations: Minimal; color expression is maximum under long cool days and nights.

CALYX

Size: Length, 2.5 to 3 cm; width, 1 to 1.5 cm.

Shape: Immature bud: oval with pointed tip.

Number of sepals: Five.

PLANT CHARACTERISTICS

Growth and duration: Bushy. Continuous for one to three years under greenhouse environment.

Branching pattern: Semi-erect, unrestricted at base of plant, induced by pinching and flower harvest.

Height: Single pinched plant, first cut — 80 to 89 cm. in Salinas, Calif. with average 13° C. minimum temperature.

Stem:

*Length.*—50 to 55 cm. from top to first vegetative lateral.

*Bending traits.*—10 to 16 degrees (SAF standards). Seldom brittle.

FOLIAGE

Occurance:

*Shape.*—Narrow, pointed.

*Length.*—9 to 11 cm.

Texture: Leathery with waxed cuticle.

Displacement: Normally curved with slight reflex; sometimes curled.

Color:

*Mature.*—Upper surface 138A.

*Mature.*—Under surface 138A.

*Immature.*—Upper surface 191A.

*Immature.*—Under surface 191A.

CHART A

COMPARISON OF ACE HIGH AND ACE

| CULTIVAR | FLOWER COLOR | AVERAGE FLOWER SIZE | AVERAGE BUDS & FLS. PER STEM | AVERAGE FLOWERING RESPONSE |
|---|---|---|---|---|
| ACE HIGH | LIGHT ORANGE EXTENSIVE SCARLET RED PICOTEE DEEPLY STRIPED AND SPOTTED | 45 to 65 mm. | 6 to 8 | MEDIUM 25 to 29 WEEKS TO FIRST PEAK CUT JULY PLANTINGS |
| ACE | LIGHT ORANGE SLIGHT SCARLET RED PICOTEE FAINTLY STRIPED AND SPOTTED | 45 to 65 mm. | 6 to 8 | MEDIUM 22 to 26 WEEKS TO FIRST PEAK CUT |

| CULTIVAR | AVERAGE PEDUNCLE LENGTH | AVERAGE PEDUNCLE STRENGTH | AVERAGE PLANT HEIGHT |
|---|---|---|---|
| ACE HIGH | MEDIUM 10 to 12 cm. | STRONG | TALL 80 to 89 cm. |
| ACE | MEDIUM 10 to 12 cm. | STRONG | TALL 72 to 81 cm. |

COMPARISONS MADE OF PINCHED, FLOWERING PLANTS GROWN AS SPRAYS WITH CENTER BUDS REMOVED IN SALINAS, CALIFORNIA

I claim:

1. A new and distinct cultivar of *Dianthus caryophyllus,* Linn., named Ace High as described and illustrated, and particularly characterized as to distinctiveness by the combined characteristics of commercial double flower type, flat, slightly reflexed form, miniature size of 45 to 65 mm. diameter, light orange with scarlet red variegated color, medium response, 6 to 8 flowers and buds showing color per stem, medium 10 to 12 cm. peduncle length, strong peduncle strength, and tall plant height.

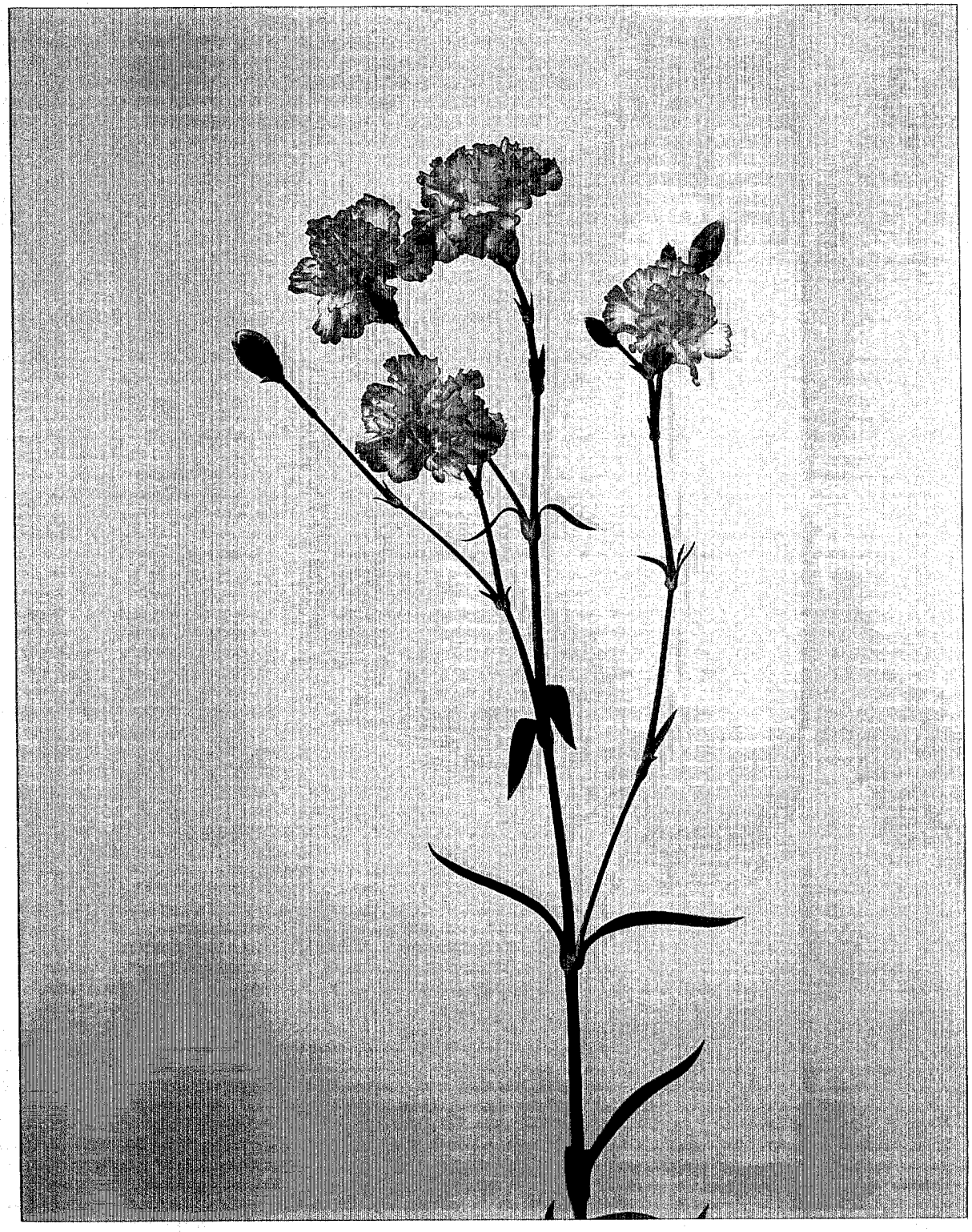

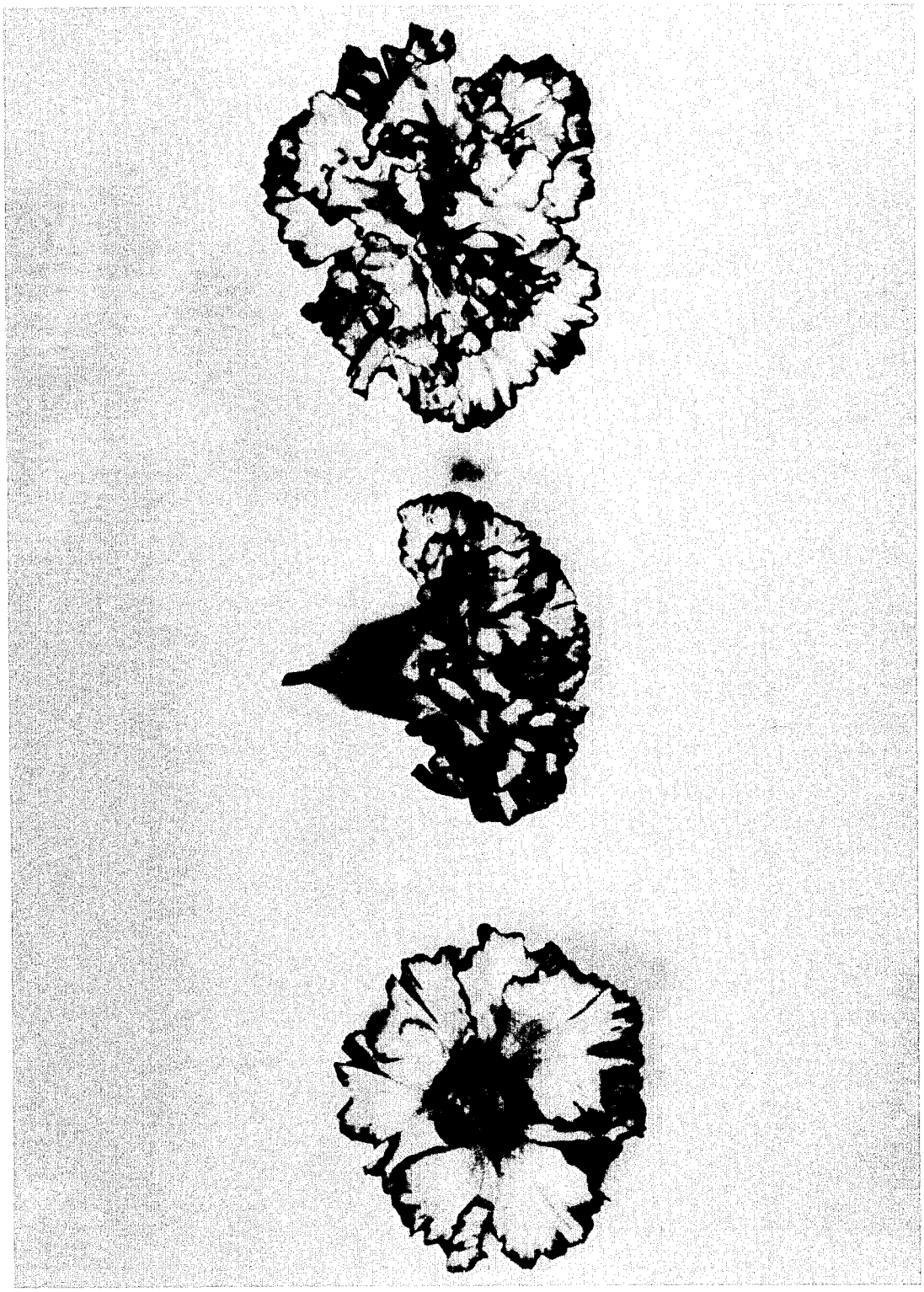

* * * * *